United States Patent [19]

Nudelman et al.

[11] Patent Number: 5,030,723
[45] Date of Patent: Jul. 9, 1991

[54] LONG-CHAIN GLYCOLIPID STRUCTURE

[75] Inventors: Edward D. Nudelman; Steven B. Levery; Mark R. Stroud; Mary Ellen K. Salvan; Sen-itiroh Hakomori, all of Seattle, Wash.

[73] Assignee: The Biomembrane Institute, Seattle, Wash.

[21] Appl. No.: 200,160

[22] Filed: May 31, 1988

[51] Int. Cl.$^5$ .......................... C07H 13/06; C07H 5/04
[52] U.S. Cl. .......................... 536/53; 536/4.1; 536/18.2; 536/55.1; 536/119
[58] Field of Search ............... 536/4.1, 53, 18.2, 119, 536/55.1

[56] References Cited

U.S. PATENT DOCUMENTS 4,857,639 8/1989 Clausen .................................. 514/54

FOREIGN PATENT DOCUMENTS 0173648 3/1986 European Pat. Off. .
0293262 11/1988 European Pat. Off. .

OTHER PUBLICATIONS

Hakomori; Ann, Rev. Biochem. 50:733–764 (1981).
Nudelman et al.; J. Biol. Chem. 257(21):12752–12756 (1982).
Hansson et al.; J. Biol. Chem. 258(7).4091–4097 (1983).
Fukushi et al.; J. Biol. Chem. 259(7):4681–4685 (1984).
Lamblin et al.; J. Biol. Chem. 259(14);9051–9056 (1984).
Fukushima et al., Cancer Res. 44:5279–4285 (1984).
Hanson et al.; J. Biol. Chem. 260(16); 9388–9342 (1985).
Fukuda et al.; J. Biol. Chem. 261(5); 7376–2383 (1986).
Hanisch et al.; Febs Lett. 200(1):42–46 (1986).
Levery et al.,; Carb. Res. 178:121–144 (1988).
Macher et al., J. Biol. Chem. 263(21):10186–10191 (1988).

*Primary Examiner*—Johnnie R. Brown
*Assistant Examiner*—Nancy S. Carson
*Attorney, Agent, or Firm*—Sughrue, Mion, Zinn, Macpeak & Seas

[57] ABSTRACT

A substantially pure unbranched ceramide polysaccharide type 2 chain compound having the following structure:

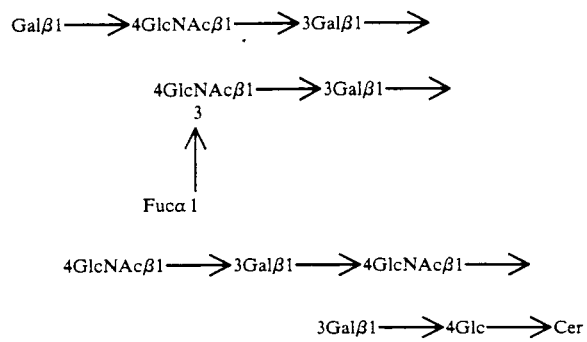

wherein Gal represents galactose, GlcNAc represents N-acetylglucosamine, Fuc represents fucose Glc represents glucose and Cer represents ceramide. A substantially pure unbranched ceramide polysaccharide type 2 chain compound having the following structure:

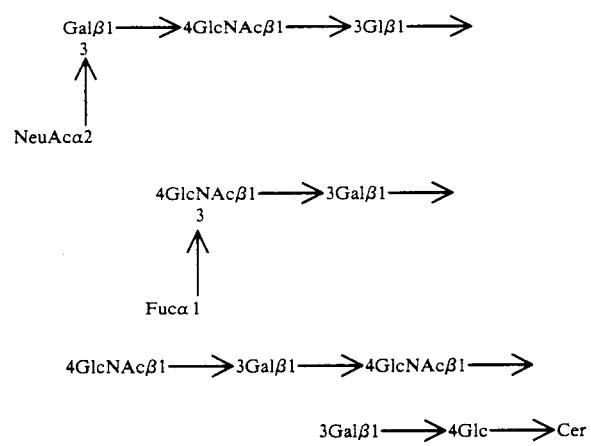

wherein Gal represents galatose, GlcNAc represents N-acetylglucosamine. Fuc represents fucose, Glc repre- (Abstract continued on next page.)

sents glucose, Cer represents ceramide and NeuAc represents sialic acid. Antibodies that are specific to portions of the above-described compounds, wherein the portions comprise the internal $\alpha 1 \longrightarrow 3$ fucosyl residue and/or the terminal sialic acid residue. Immuogens for producing antibodies to the above-described compounds or portions thereof. A method of actively immunizing against tumors that express the above-described compounds.

2 Claims, 7 Drawing Sheets

LONG-CHAIN GLYCOLIPID STRUCTURE

FIELD OF THE INVENTION

The present invention relates to new differentiation-dependent tumor-associated antigens, and in particular the present invention relates to an unbranched ceramide hendecasaccharide type 2 chain which has an internal $\alpha 1 \rightarrow 3$ fucosyl residue and to a sialylated derivative thereof which have been isolated and characterized from human colonic cancer tissues. The structures constitute an important group of tumor antigens and can be used as immunogens to produce polyclonal or monoclonal antibodies that bind to the structures or to raise antibodies in vivo against the structures in order to actively immunize a subject against tumors that express such differentiation-dependent tumor-associated antigens. The present invention also relates to polyclonal and monoclonal antibodies that bind to specific antigenic portions within the structures.

BACKGROUND OF THE INVENTION

Essentially all known human cancers have been characterized by aberrant glycosylation occurring in lipids (glycosphingolipids) or in proteins (glycoproteins) expressed at the cell surface membrane (Hakomori, S. (1985) Cancer Res. 45, 2405-2414). Aberrant glycosylation in human cancer has been indicated by the presence of a large quantity of novel fucosylated glycolipids detected by chemical analysis (Hakomori, S. and Andrews, H. (1970) Biochim. Biophys. Acta 202, 225-228; Yang, H.-J., and Hakomori, S. (1971) J. Biol. chem. 246, 1192-1200; Hakomori, S. et al. (1984) J. Biol. Chem. 259, 4672-4680; Nudelman, E. et al. (1986) J. Biol. Chem. 261, 11247-11253), and by the fact that many monoclonal antibodies selected by preferential or specific reactivity with human cancer have been characterized as being directed to glycophingolipids or glycoproteins (Nudelman, E., et al., (1986) J. Biol. Chem. 261, 11247-11253; Magnani, J. L. et al. (1982) J. Biol. Chem. 257, 14365-14369; Fukushi, Y., et al. (1984) J. Biol. Chem. 259, 4681-4685 and Fukushi, Y. et al. (1984) J. Biol. Chem. 259, 10511-10517; see Hakomori, S. (1985) Cancer Res. 45, 2405-2414 and Hakomori, S. (1984) Ann. Rev. Immunol. 2, 103-126 for a review). The characteristic change occurring in the most common human cancers (i.e. gastrointestinal, breast and lung cancers) is the accumulation of large quantities of fucosylated type 1 and 2 chains (Le$^a$, Le$^x$, di- or trimeric Le$^x$, Le$^b$, Le$^y$) or their sialylated derivatives (sialyl Le$^x$, sialyl di- or trimeric Le$^x$, sialyl Le$^a$) defined by various monoclonal antibodies (Yang. H.-J. and Hakomori, S. (1971) J. Biol. Chem. 246, 1192-1200; Hakomori, S. et al. (1986) J. Biol. Chem. 259, 4672-4680; Nudelman, E. et al., (1986) J. Biol. Chem. 261, 11247-11253; Magnani, J. L. et al. (1982) J. Biol. Chem. 257, 14365-14369g; Fukushi, Y. et al. (1984) J. Biol. Chem. 259, 4681-4685; Fukushi, Y. et al. (1984) J. Biol. Chem. 259, 10511-10517; see Hakomori, S. (1984) Ann. Rev. Immunol. 2, 103-126 for a review).

Because such fucosylated molecules could be useful for preparing antibodies directed to human cancer associated antigens and even as a vaccine for immunization against some cancers, isolation and characterization of such fucosylated structures and their antigenic determinants is an important aspect of cancer research.

SUMMARY OF THE INVENTION

Accordingly, one object of the present invention is to provide structural information about two new fucosylated glycolipid compounds which have not been previously known, obtained in purified form or synthetically produced.

A second object of the present invention is to provide in vivo applications of these fucosylated glycolipid compounds to produce antibodies to cancer associated antigens and to actively immunize subjects against tumor cells expressing these cancer associated antigens.

These and other objects have been accomplished by providing a substantially pure unbranched ceramide polysaccharide type 2 chain compound having the following structure:

wherein Gal represents galactose, GlcNAc represents N-acetylglucosamine, Fuc represents fucose, Glc represents glucose and Cer represents ceramide.

The present invention also provides a sialylated derivative of the above-described compound which is a substantially pure unbranched ceramide polysaccharide type 2 chain compound having the following structure:

wherein Gal represents galactose. GlcNAc represents N-acetylglucosamine, Fuc represents fucose, Glc represents glucose Cer represents ceramide and NeuAc represents sialic acid.

In a further aspect, the present invention provides antibodies that are specific to portions of the above-described compounds, which portions comprise the internal $\alpha 1 \rightarrow 3$ fucosyl residue and/or, in the case of the sialylated compound, the terminal sialic acid residue.

In an even further aspect, the present invention provides immunogens for producing antibodies specific to the above-described compounds or portions thereof which comprise: (a) the above-described compounds or antigenic fragments thereof and (b) an adjuvant.

In still another aspect, the present invention provides a method of actively immunizing against tumors that express the above-described compounds which comprises vaccinating a subject with a vaccine comprising the above-described compounds or antigenic fragments thereof.

BRIEF DESCRIPTION OF THE DRAWINGS

FIG. 1 is a HPTLC (high performance thin-layer chromatography) pattern of monosialogangliosides of pooled human colonic cancer. Panel A: The TLC was developed in chloroform-methanol-water (50:40:10 v/v/v) containing 0.5% $CaCl_2$ by weight. Panel B: The TLC was developed in chloroform-methanol-water (50:47:14 v/v/v) containing 0.05% $CaCl_2$ by weight. Panels A and B: Lane 1, total monosialoganglioside fraction of pooled colonic cancer. Lanes 2–9 are HPLC (high performance liquid chromatography) fractions 3–6, 7–14, 15–33, 34–45, 46–56, 57–60, 61–62, and 63–65, respectively, as described in the Example. Lane 10 is $VI^3NeuAcV^3FucIII^3FucnLc_6$ (glycolipids are abbreviated according to the recommendations of the IUPAC Commission on Nomenclature (IUPAC-IUB Commission on Biochemical Nomenclature (1977) *Lipids* 12, 455–463), but the suffix OseCer is omitted.). Lanes 11–18 are fractions 66–68, 69–74, 75–79, 80–84, 85–95, 96–110, 111–120, and 121–153, respectively, as described in the Example. The arrow indicates the sialylated compound of the present invention. $Z_1$ is $VII^3FucnLc_8$, $Z_2$ is $V^3FucVII^3FucnLc_8$ and $Z_3$ is $III^3FucV^3FucVII^3FucnLc_8$.

FIG. 3 shows the TLC behavior of purified monosialoganglioside showing positive ACFH-18 reactivity. Panel A, developed with 2-propanol-acetonitrile-water (67:10:23 v/v/v) containing 0.05% $CaCl_2$ (by weight). Panel B, developed with N-propanol-30% aqueous ammonium hydroxide (60:39 v/v). Panel C, developed with chloroform-methanol-water (50:47:13 v/v/v) containing 0.05% $CaCl_2$ by weight. Lane 1, purified standard $VI^3NeuAcV^3FucIII^3FucnLc_6$ (FH6 antigen). Lane 2, monosialoganglioside fraction of colonic cancer. Lane 3, fractions 69–74 from first-step HPLC containing the sialylated compounds of the present invention. Lane 4, purified sialylated compound of the present invention by second-step HPLC followed by preparative HPTLC corresponding to lower band. Lane 5, the same preparative step corresponding to upper band. Lane 6, monosialoganglioside fraction of human erythrocytes.

FIG. 4 is a resolution enhanced 500 MHz $^1$H-NMR spectrum of combined faster and slower migrating fractions containing the sialylated compound of the present invention, obtained at 328±2 K. A, upfield region; B, downfield region. Arabic numerals refer to ring protons of residues designated by Roman numerals or capital letters in the corresponding structure; R refers to protons of sphingosine backbone only; Cis refers to vinyl protons of unsaturated fatty acids; nFa refers to protons of nonhydroxylated fatty acids. Impurity peaks are deleted at about 4.99 and 1.38 p.p.m. and marked X at 4.23, 1.77, 1.08 and 1.05 p.p.m.

FIG. 7 is an HPTLC pattern of the sialylated compound of the present invention. i.e. $X^3NeuAcVII^3FucnLc_{10}$, and the enzymatic degradation product derived therefrom. Panel A, stained by 0.2% orcinol in 2M sulfuric acid. Panel B, stained with ACFH-18 antibody. Panel C, stained with an anti-Le$^x$ antibody. Panel D, stained with anti-N-acetyllactosamine antibody 1B2. Lane 1, upper neutral glycolipid from O erythrocytes. Lane 2, purified sialylated compound of the present invention. Lane 3, sialylated compound of the present invention treated with sialidase. Lane 4, sialylated compound of the present invention treated with sialidase followed by jackbean $\beta$-galactosidase. Lane 5, sialylated compound of the present invention treated with sialidase, jackbean $\beta$-galactosidase and jackbean $\beta$-N-acetylhexosaminidase. Panel C, lane 6, $Z_1$ glycolipid fraction from O erythrocytes.

DETAILED DESCRIPTION OF THE INVENTION

The substantially pure compounds of the present invention can be obtained by isolating the structures from appropriate tumor cells.

Specifically, the compounds can be isolated from any cancer tissue that expresses the compounds, such as human colonic cancer tissue. Human gastric cancer tissue is also considered to express the compounds.

The compounds of the present invention have a slower TLC mobility than sialosyl decaosylceramide (Viii$^3$NeuAcnLc$_{10}$) or nordecaosylceramide (nLc$_{10}$) and thus can be purified by two-step HPLC in an isopropanol-hexane-water system followed by final separation and purification by preparative HPTLC using development with a very polar solvent system as described in detail in the Example.

For isolating the sialylated compound of the present invention, the ganglioside fraction from cancer tissue is used in the following scheme. For isolating the desialylated compound of the present invention, the neutral glycolipid fraction from cancer tissue is used in the following scheme. The ganglioside fraction and the neutral glycolipid fraction are obtained from the cancer tissue by known methods (See, for example. Hakomori, S. (1983) Chemistry of Glycospingolipids, Handbook of Lipid Research, Vol. 3, Plenum Press, N.Y. pp. 1-165; Hakomori, S. et al. (1984) *J. Biol. Chem.* 259, 4681-4685 and Fukushi, Y. et al. (1984) *J. Biol. Chem.* 159, 10500-10517).

In order to perform the first-step HPLC. the fraction is dried and dissolved in a suitable solvent (e.g. chloroform-methanol (2:1 v/v) with 6% water by volume). The sample is applied to a porous silica gel column (e.g. Iatrobeads 6RS 8010—a porous silica gel manufactured by Iatron Chemical Co., Kanda, Tokyo, Japan) and a series of gradient elutions with different solvents is performed followed by isocratic elution.

The fractions from the first-step HPLC that contain the compounds of the present invention are identified by positive immunostaining with the monoclonal antibody ACFH-18 (Abe, K., et al. (1983) *J. Biol. Chem.* 258, 11793-11797). Specifically, an aliquot of each fraction is analyzed by HPTLC and then immunostained with monoclonal antibody ACFH-18 by known methods.

In the second-step HPLC, the fractions containing the major ganglioside showing positive immunostaining are pooled and subjected to another analytical column of a porous silica gel (e.g. Iatrobeads 6RS 8010). Gradient elution is performed with two solvents and the fractions containing the compounds of the present invention are again identified by positive immunostaining with monoclonal antibody ACFH-18.

Final purification of the compounds is accomplished by preparative HPTLC on plates which are developed with highly polar solvents such as those described in the Example.

Bands containing the compounds of the present invention are identified by positive immunostaining with monoclonal antibody ACFH-18. The bands containing the compounds are scraped off of the plate and the compounds extracted in isopropanol-hexane-water (50:25:20 v/v/v) with sonication by known methods (Nudelman, E., et al (1986) *J. Biol. Chem.* 261, 11247-11253; Kannagi, R., et al (1982) *J. Biol. Chem.* 257, 14865-14874).

As an alternative to isolating the compounds of the present invention from cancer tissue, the compounds should be able to be made synthetically by methods readily determined by the skilled artisan.

The substantially pure compounds of the present invention can be characterized by NMR spectrometry, positive ion fast atom bombardment mass spectrometry and electron impact limited mass chromatography as illustrated in the Example.

Once obtained in substantially pure form, the compounds of the present invention can be used as immunogens to prepare polyclonal or monoclonal antibodies to the entire structure of each compound (similar to the monoclonal antibody ACFH-18 described above) or specific to portions of the compounds including portions which contain the $\alpha 1 \rightarrow 3$ fucosyl residue and/or the terminal sialic acid residue, in the case of the sialylated compound.

Both polyclonal and monoclonal antibodies specific to the above-described portions of the compounds of the present invention which contain the $\alpha 1 \rightarrow 3$ fucosyl residue and/or the terminal sialic acid residue are novel and have never before been described and thus, these polyclonal and monoclonal antibodies constitute another aspect of the present invention.

The polyclonal or monoclonal antibodies can be established by conventional methods after immunization of suitable hosts with the immunogen (Hakomori S., Methods of Enzymology, Vol. 28, 232-236 (1973) and Young. W. W. et al. (1979) *J. Expt. Med.* 150, 1008-1019).

For producing antibodies specific to the entire structure of the desialylated compound of the present invention or specific to portions of the desialylated compound, the immunogen can be the full length desialylated compound or an antigenic fragment of the compound mixed with a suitable adjuvant. Of course, in order to produce antibodies specific to a portion of the desialylated compound containing the $\alpha 1 \rightarrow 3$ fucosyl residue, the immunogen will need to include a portion of the compound having the $\alpha 1 \rightarrow 3$ fucosyl residue.

Similarly, for producing antibodies specific to the entire structure of the sialylated compound of the present invention or specific to fragments of the sialylated compound, the immunogen can be the full length sialylated or desialylated compound or an antigenic fragment of either compound mixed with a suitable adjuvant. Further, in order to produce antibodies specific to a portion of the sialylated compound containing the $\alpha 1 \rightarrow 3$ fucosyl residue the immunogen will need to include a portion of either compound having the $\alpha 1 \rightarrow 3$ fucosyl residue and in order to produce antibodies specific to a portion of the sialylated compound containing the terminal sialic acid residue, the immunogen will need to include a portion of the sialylated compound having the terminal sialic acid residue.

Suitable adjuvants for the immunogens can readily be determined by the skilled artisan and include, for example, bacteria onto which the compound is adsorbed and virus membranes onto which the compound is adsorbed.

The present invention also provides a method of actively immunizing against tumors that express the desialylated compound of the present invention which comprises vaccinating a subject with a vaccine comprising the desialylated compound or an antigenic fragment thereof and a method of actively immunizing against tumors that express the sialylated compound which comprises vaccinating a subject with a vaccine comprising the desialylated compound or an antigenic fragment thereof or with a vaccine comprising the sialylated compound or an antigenic fragment thereof.

In addition to the compounds of the present invention or antigenic fragments of the compounds, the vaccine will normally include suitable pharmaceutically acceptable carriers, diluents or excipients which can readily be determined by the skilled artisan.

Suitable methods of administration of the vaccine may also be readily determined by the skilled artisan.

Suitable doses of the vaccine to be administered may vary depending upon the age of the subject and mode of administration but can readily be determined by the skilled artisan.

In general, a suitable dose for intradermal injection to humans is about 20 to 50 µg of the compound or antigenic fragment coated on 1 to 2 mg of BCG at one time.

EXAMPLE

The present invention will now be described by reference to a specific example which is not meant to be limiting.

Unless otherwise specified, all percents, ratios, etc. are by volume.

Monoclonal Antibodies and Immunological Assays

The monoclonal antibody ACFH-18 was established by conventional methods after immunization of Balb/c mice with human gastric cancer cell line MKN74. (Fukushi, Y., et al. (1984) *J. Biol. Chem.* 259, 4681-4685 and Abe, K., et al. (1983) *J. Biol. Chem.* 258, 11793-11797). ACFH-18 reacts preferentially with human gastrointestinal adenocarcinoma, but also reacts with a limited number of crypt cells in gastric foveolae and intestinal crypt cells. Further, the ACFH-18 reactivity to gastric cancer depends on the state of differentiation. The antibody reacts with a series of glycolipids with extremely low mobility in both the ganglioside and neutral glycolipid fractions after performing thin-layer chromatography (TLC).

The reactivity of monoclonal antibody ACFH-18 with various glycolipids was assayed by TLC immunostaining using Whatman HPTLC plates (HP-KF, Maidstone, England) by a modified version (Kannagi, R., et al (1982) *J. Biol Chem.* 257, 4438-4442 and Kannagi, R., et al (1982) *J. Biol. Chem.* 257, 14865-14874) of the method originally described by Magnani et al. (Magnani, J. L. et al. (1980) *Anal. Biochem,* 109, 399-402), and by solid-phase radioimmunoassay as previously described (Kannagi, R. et al. (1983) *Cancer Res.* 43, 4997-5005).

Other antibodies used as reagents for characterization of antigens were prepared as follows. Anti-Le$^x$ FH2 was prepared according to he method disclosed in Fukushi, Y., et al. ((1984) *J. Biol. Chem.* 259, 4681-4685). Anti-N-acetyllactoseamine 1B2 was prepared according to the method disclosed in Young, W. W. Jr., et al. ((1981) *J. Biol. Chem.* 256, 10967-10972).

Glycolipid Preparation

Since the glycolipid fraction showing positive immunostaining with ACFH-18 antibody, i.e., the glycolipid fraction containing the sialylated compound of the present invention had TLC mobility slower than decaosylceramide, the compound was purified by two-step HPLC in an isopropanol-hexane-water system followed by final separation and purification performed by preparative HPTLC using development with a very polar solvent system (see following section).

Separation of Sialylated Compound of Present Invention by Two-Step HPLC and Preparative HPTLC First-step HPLC: The ganglioside fractions of 9 colonic cancer tissues were evaporated in a rotary evaporator and further dried in vacuo, dissolved in 10 ml of chloroform-methanol (2:1 v/v) with addition of 6% water by volume, and sonicated. The solution was applied to a 1×50 cm Iatrobeads 6RS 8010 column pre-equilibrated with isopropanol-hexane-water (55:40:5 v/v/v), and eluted with the same solvent for 160 min with a flow rate of 0.5 ml/min during the first 40 min and with a flow rate of 2.0 ml/min during the remaining 120 min. Gradient elution with isopropanol-hexane-water (55:40:5 v/v/v) to (55:34:11 v/v/v) was applied from 161 min to 220 min with a flow rate of 0.5 ml/min. Subsequently, gradient elution changed from isopropanol-hexane-water (55:34:11 v/v/v) to (55:20:25 v/v/v) from 221 min to 480 min. Isocratic elution continued until 600 min with a constant flow rate of 0.5 ml/min. Effluent (2 ml/fraction) was collected over a fraction collector, and a 5 µl aliquot of each fraction was analyzed on HPTLC and immunostained with ACFH-18 and other appropriate antibodies in order to determine the contents of each fraction.

Figure 1:
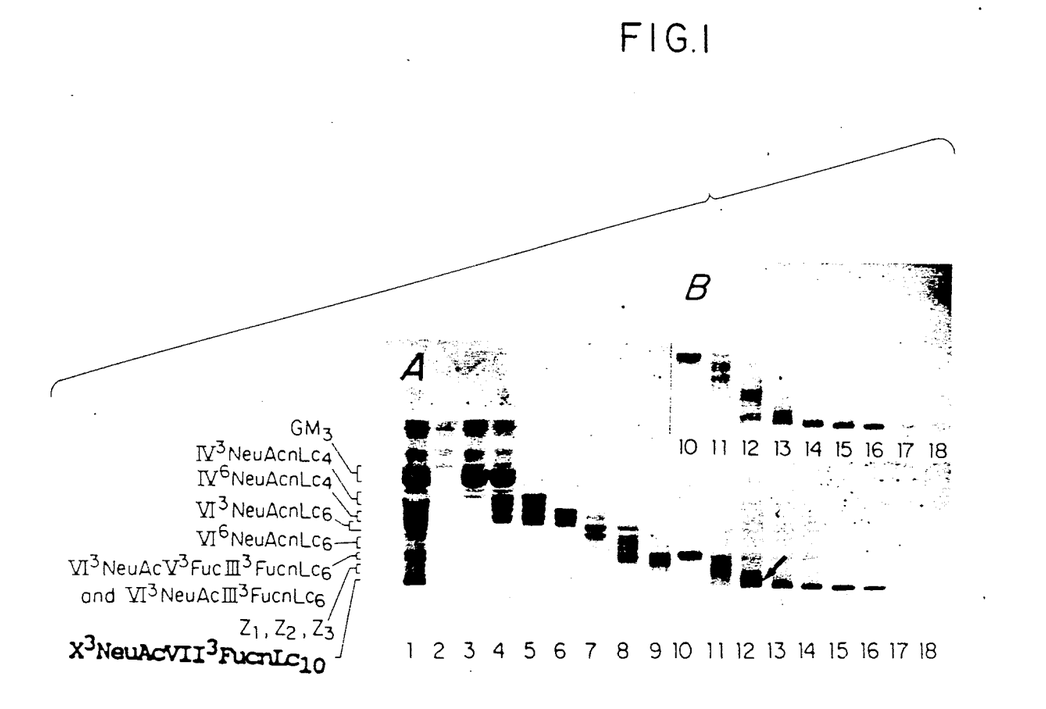

The results are shown in FIG. 1.

In FIG. 1, Panel A shows the pattern after TLC developed in chloroform methanol-water (50:40:10 v/v/v) containing 0.05% CaCl$_2$ by weight and Panel B shows the pattern after TLC developed in chloroform methanol-water (50:47:14 v/v/v) containing 0.05% CaCl$_2$ by weight. Lane 1 is the pattern for the total monoganglioside fraction of pooled colonic cancer, and lane 10 is the pattern for the standard, VI$^3$NeuAcV-$^3$FucIII$^3$FucnLc$_{10}$. Fractions 3-14 (lanes 2 and 3) contained GM$_3$. Fractions 15-33 (lane 4) contained GM$_3$ plus small quantities of IV$^3$NeuAcnLc$_4$ and IV$^6$NeuAcnLc$_4$. Fractions 34-45 (lane 5) contained IV$^3$-NeuAcnLc$_4$ and IV$^6$NeuAcnLc$_4$ as major components. Fractions 46-56 (lane 6) contained almost exclusively IV$^6$NeuAcnLc$_4$. Fractions 57-60 (lane 7) contained VI$^3$NeuAcnLc$_6$. Fractions 61-62 (lane 8) contained VI$^6$NeuAcnLc$_6$. Fractions 63-65 (lane 9) contained VI$^3$NeuAcV$^3$FucIII$^3$FucnLc$_6$ and VI$^6$NeuAcIII$^3$-FucnLc$_6$ (6C ganglioside). Fractions 66-68 (lane 11) contained sialyl Z$_1$ glycolipid (VII$^3$NeuAcVII$^3$-FucnLc$_8$). Fractions 69-74 (lane 12) contained the sialylated compound of the present invention. The immobile positive band containing the compound of the present invention in lane 12 of Panel A was separated into multiple components when the TLC was developed under the conditions of Panel B. More polar fractions eluted subsequently, i.e., fractions 75-79 (lane 13), 80-84 (lane 14), 85-95 (lane 15), 96-110 (lane 16), 111-120 (lane 17), and 121-153 (lane 18), which contained minor slow-migrating components and that were ACFH-18 positive (FIG. 1A, B). The glycolipids contained in the last 5 fractions hardly migrated on HPTLC, even with a polar solvent, indicating that these components are highly complex.

Second-step HPLC: The major ganglioside showing an ACFH-18 positive reaction separated on first-step HPLC was pooled and subjected to double analytical columns (Iatrobeads 6RS 8010, 0.4×30 cm for each column), pre-equilibrated with isopropanol-hexane-water (55:40:5 v/v/v). Gradient elution was started from this solvent and ended with isopropanol-hexanewater (55:32:13 v/v/v) during the first 300 minutes, then the solvent was changed to isopropanol-hexane-water (55:30:15 v/v/v) from 301 min to 400 min. with a flow rate of 0.5 ml/min. The effluent (1 ml per tube) was collected over a fraction collector, and a 5 μl aliquot of each fraction was analyzed on HPTLC and immunostained with ACFH-18 and other appropriate antibodies in order to determine the contents of each fraction.

Figure 2A:
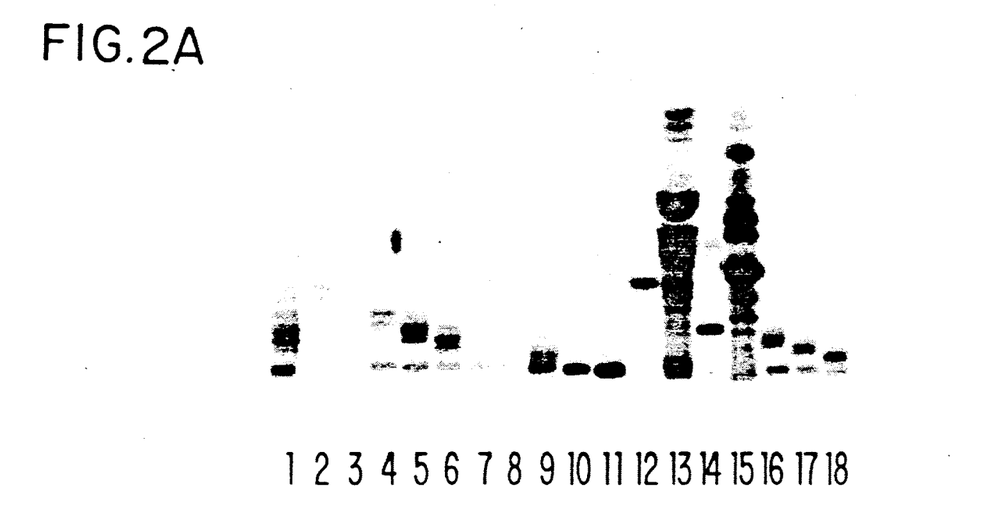
FIG. 2 shows the pattern produced by various ganglioside fractions and upper neutral glycolipids semipurified by second-step HPLC as described in the Example. Panel A: HPTLC pattern revealed by 0.2% orcinol and 2M sulfuric acid. Lane 1, fractions 69–74 obtained from first-step HPLC. Lanes 2–8, various fractions obtained from second-step HPLC of fractions 69–74. Lanes 2 and 3 are fractions 1–12 and 13–22 before the start of gradient elution. Lanes 4–8 are fractions obtained after the start of gradient elution: i.e., fractions 1–12, 13–22, 23–33, 34–40 and 41–53, respectively. Lanes 9–11 are fractions 75–79, 80–84 and 85–95 from the first-step HPLC, respectively. Lane 12, $VI^3NeuAcV^3FucIII^3FucnLc_6$. Lane 13, monosialonganglioside fraction of pooled human colonic cancer. Lane 14, purified sialylated compound of the present invention. Lane 15, upper neutral glycolipid from tumors. Lanes 16–18, upper neutral glycolipid fraction separated on HPLC under the same conditions as applied for HPLC of the monosialoganglioside fraction. Lane 16, fractions 44–46. Lane 17, fractions 47–49. Lane 18, fractions 50–51. Panel B: immunoblotting pattern of the same HPTLC with antibody ACFH-18.
Figure 2B:
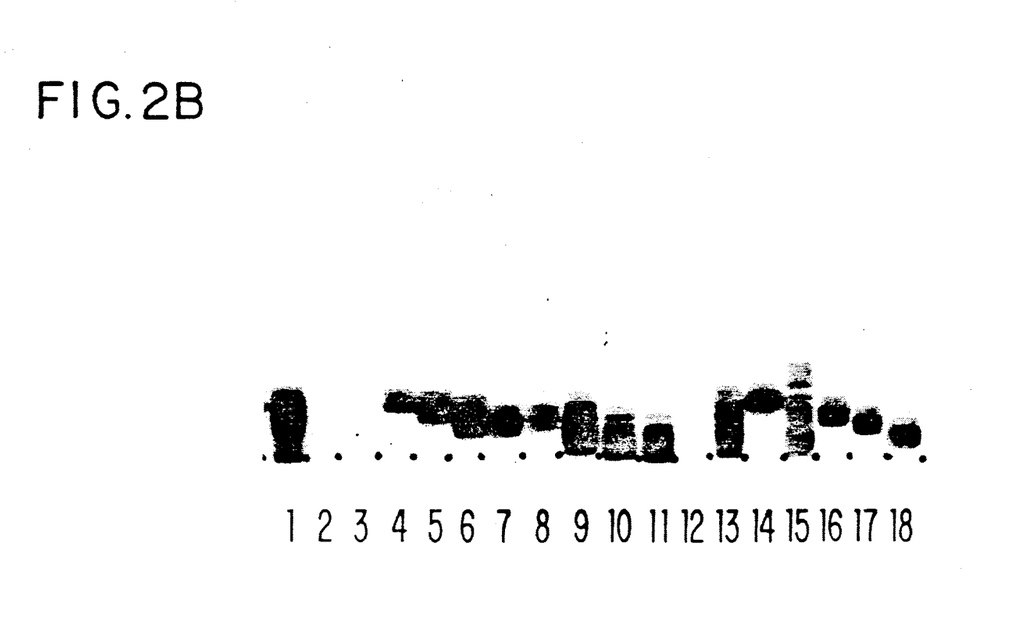

The results are shown in FIG. 2.

Panel A shows the HPTLC pattern revealed by 0.2% orcinol and 2M sulfuric acid. Fractions 69-74 (lane 1) were obtained from first-step HPLC. Lanes 2-8 are various fractions obtained from second-step HPLC of fractions 69-74. Lanes 2 and 3 are fractions 1-12 and 13-22 before the start of gradient elution. Lanes 4-8 are fractions obtained after the start of gradient elution: i.e., fractions 1-12, 13-22, 23-33, 34-40 and 41-53, respectively. Lanes 9-11 are fractions 75-79, 80-84 and 85-95 from the first-step HPLC respectively. Lane 12 is the standrd VI$^3$NeuAcV$^3$FucIII$^3$FucnLc$_6$. Lane 13 is a monosialoganglioside fraction of pooled human colonic cancer. Lane 14 is a purified sialylated compound of the present invention. Lane 15 is upper neutral glycolipid from tumors. Lanes 16-18 are the upper neutral glycolipid fraction separated on HPLC under the same conditions as applied for HPLC of monosialogangliosides. Lane 16 is fractions 44-46. Lane 17 is fractions 47-49. Lane 18 is fractions 50-51. Panel B shows the immunoblotting pattern of the same HPTLC with antibody ACFH-18. Immunoblotting was conducted by known methods (Magnani, J. F. et al. (1980) *Analytical Biochem.* 109, 399-402 and Abe et al. (1983) *J. Biol. Chem.* 258. 11793-11797). The sialylated compounds of the present invention were in fractions 13-22 (lane 5) and 23-33 (lane 6). These two major fractions have almost identical HPTLC mobility but different HPLC retention times.

Preparative HPTLC: ACFH-18 positive ganglioside fractions from the second-step HPTLC were pooled (fractions 13-22 and 23-33) and final purification of the resulting fraction was performed by preparative HPTLC on EM Science HPTLC plates, which were developed with highly polar solvents such as chloroform-methanol-water (50:47:14 v/v/v) containing 0.05% CaCl$_2$ by weight as a final concentration, chloroform-methanol-water-28% aqueous ammonia (50:45:10:8 v/v/v/v), N-propanol-water-28% aqueous ammonia (50:20:15 v/v/v), or isopropanol-acetonitrile-water (67:10:23 v/v/v) containing 0.05% CaCl$_2$ by weight as a final concentration. Bands separated and showing positive immunostaining with ACFH-18 as indicated by a guide TLC lane and by Primulin spray (Skipski, V. P. (1975) *Meth. Enzymol.* 35, 396-425) were scraped and extracted by sonication with isopropanol-hexane-water (50:25:20 v/v/v) as described previously (Nudelman, E. et al. (1986) *J. Biol. Chem.* 261, 11247-11253 and Kannagi, R., et al (1982) *J. Biol. Chem.* 257, 14865-14874).

Figure 3A:
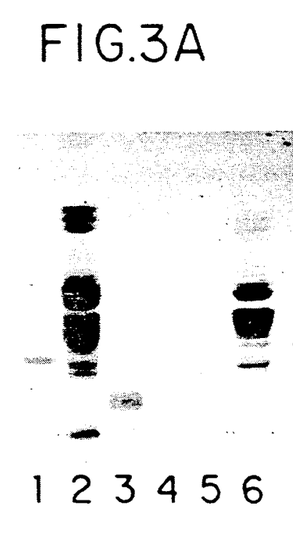
Figure 3B:
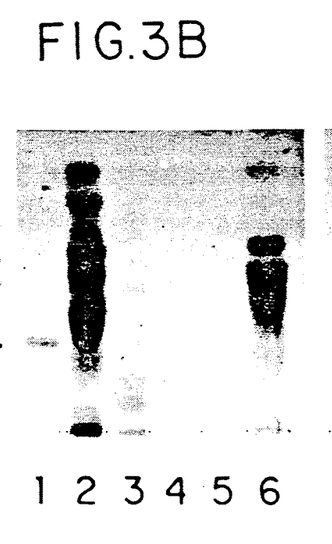
Figure 3C:
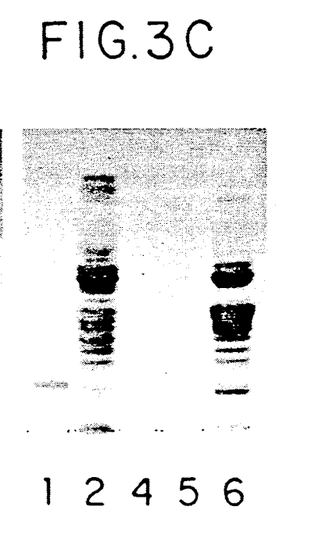

The results are shown in FIG. 3.

FIG. 3 shows that two apparently homogenous glycolipid fractions having slightly different HPTLC mobilities were thus obtained (lanes 4 and 5).

From the neutral glycolipid fraction, a series of slow-migrating compounds was also separated by HPLC. The major fraction was further purified by HPTLC with a polar solvent. The fastest-migrating component of ACFH-18 positive bands had the same mobility as ceramide hendecaosylceramide, and had an asialo core of the sialylated compound. This was the desialylated compound of the present invention.

Glycolipid Characterization

NMR Spectrometry—500 MHz proton nuclear magnetic resonance ($^1$H-NMR) spectra were recorded with a Bruker AM-500 spectrometer equipped with an Aspect 3000 computer and pulse programmer, operating in the Fourier transform mode with quadrature detection. Spectra were recorded at 328±2K (Levery, S. B. et al. (1986) *Carbohydr. Res.* 151, 311-328) on deuterium-exchanged samples dissolved in 0.4 ml of dimethylsulfoxide-d$_6$ containing 2% D$_2$O (Dabrowski, J., et al., (1980) *Biochemistry* 19, 5652-5658) and 1% tetramethylsilane as a chemical shift reference. Other parameters and data treatment were described previously (Levery, S. B. et al., *Carbohydr. Res.* 151, 311-328).

Figure 4A:
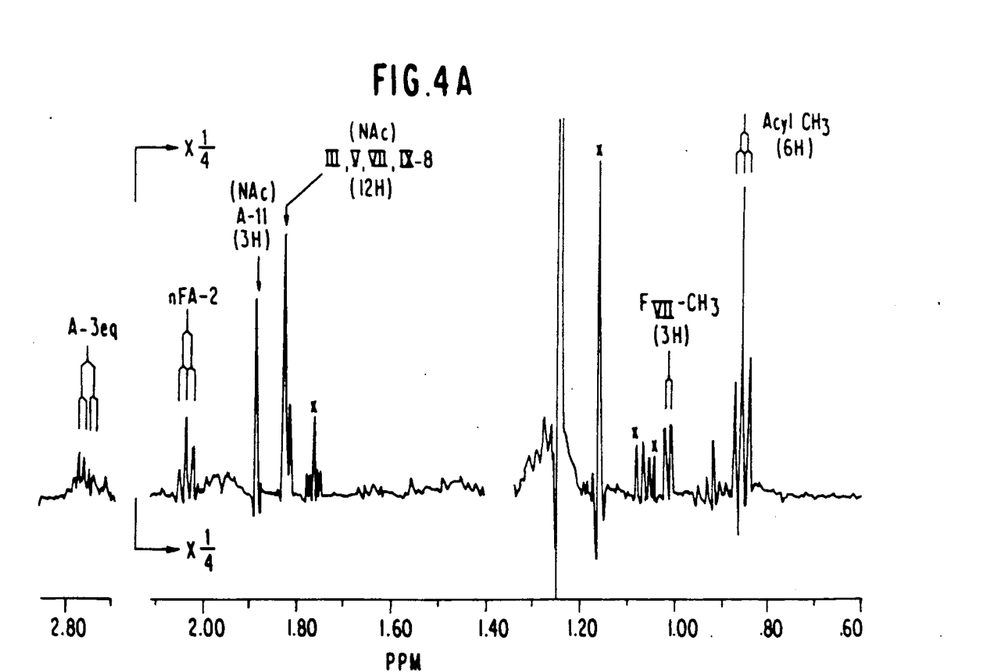
Figure 4B:
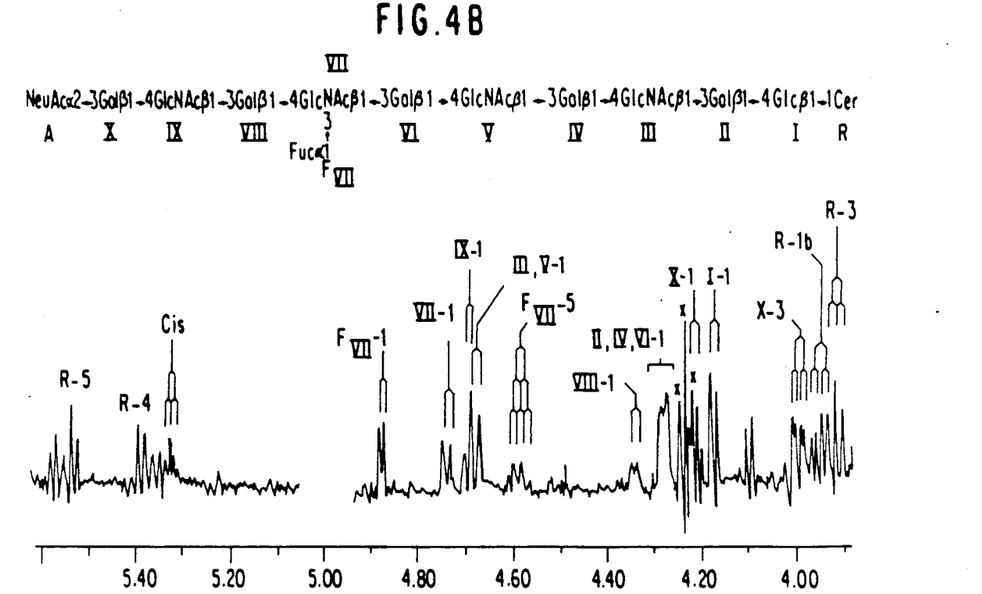

The results are shown in FIG. 4.

FIG. 4 is the $^1$H-NMR spectrum of the combined faster and slower migrating fractions containing the sialyated compounds of the present invention, taken at 328K in DMSO-d$_6$/D$_2$O 98:2 v/v.

Tables I, II and III give a partial list of resonances for a group of relevant structures obtained under the same conditions.

TABLE I

Chemical shifts (ppm from tetramethylsilane) of glycosyl H-1 resonances and coupling constants (Hz) for glycolipids$^a$ in dimethylsulfoxide-d$_6$ at 328 ± 2 K Galβ1 ⟶ 4GlcNAcβ1 ⟶ 3Galβ1 ⟶ 4GlcNAcβ1 ⟶ 3(Galβ1 ⟶ 4GlcNAcβ1 ⟶ 3)$_n$Galβ1 ⟶ 4Glcβ1 ⟶ 1Cer Fucα1 ⟶ 3      Fucα1 ⟶ 3

| | H-1 | H-1 | H-1 | H-1 | H-1 | H-1 | H-1 | H-1 | H-1 |
|---|---|---|---|---|---|---|---|---|---|
| 1  n = 0, —       | 4.228(7.3) | —          | 4.682(8.5) | 4.280(7.9) | —          | 4.682(8.5) | —          | —          | 4.280(7.9) | 4.172(7.9) |
| 2  n = 0, x = 6   | 4.240(7.3) | —          | 4.714(8.5) | 4.282(6.7) | —          | 4.678(7.9) | —          | —          | 4.282(6.7) | 4.171(7.9) |
| 3  n = 0, x = 3   | 4.212(7.9) | —          | 4.662(7.3) | 4.273(7.3) | —          | 4.678(7.9) | —          | —          | 4.277(7.9) | 4.171(7.9) |
| 4  n = 0, —       | 4.231(7.3) | —          | 4.710(8.5) | 4.342(7.3) | 4.875(3.7) | 4.748(7.9) | —          | —          | 4.279(7.3) | 4.221(7.9) |
| 5  n = 0, x = 6   | 4.245(7.3) | —          | 4.738(7.9) | 4.349(7.3) | 4.878(3.7) | 4.738(7.9) | —          | —          | 4.278(7.3) | 4.220(7.9) |
| 6  n = 2, x = 3   | 4.214(7.9) | —          | 4.692(6.7) | 4.340(6.7) | 4.875(4.3) | 4.739(7.9) | 4.277(7.3) | 4.676(7.9) | 4.277(7.3) | 4.170(7.3) |
| 7  n = 0, x = 3   | 4.301(7.3) | 4.875(3.7) | 4.726(7.9) | 4.345(6.7) | 4.875(3.7) | 4.739(7.9) | —          | —          | 4.276(7.9) | 4.222(7.9) |

$^a$1 = nLc$_6$Cer; 2 = VI$^6$NeuAcnLc$_6$Cer; 3 = VI$^3$NeuAcnLc$_6$Cer; 4 = III$^3$FucnLc$_6$Cer; 5 = III$^3$FucVI$^6$NeuAcnLc$_6$Cer; 6 = VII$^3$FucX$^3$NeuAcnLc$_{10}$Cer; 7 = III$^3$V$^3$Fuc$_2$VI$^3$NeuAcnLc$_6$Cer

TABLE II

Chemical shifts (ppm from tetramethylsilane) of Fuc H-5, $CH_3$, NeuAc, and GlcNAc NAc resonances for glycolipids[a] in dimethylsulfoxide-$d_6$ at 328 ± 2 K NeuAcα2 $\longrightarrow$ XGalβ1 $\longrightarrow$ 4GlcNAcβ1 $\longrightarrow$ 3Galβ1 $\longrightarrow$ 4GlcNAcβ1 $\longrightarrow$ 3Galβ1 $\longrightarrow$ R Fucα1 $\longrightarrow$ 3          Fucα1 $\longrightarrow$ 3

| | | NAc | H-5 | H-6 | NAc | H-5 | H-6 | NAc |
|---|---|---|---|---|---|---|---|---|
| 1 | — | — | — | — | 1.821 | — | — | 1.821 |
| 2 | x = 6 | 1.876 | — | — | 1.840 | — | — | 1.822 |
| 3 | x = 3 | 1.886 | — | — | 1.823 | — | — | 1.823 |
| 4 | — | — | — | — | 1.820 | 4.588 | 1.013 | 1.820 |
| 5 | x = 6 | 1.876 | — | — | 1.832 | 4.589 | 1.014 | 1.821 |
| 6 | x = 3 | 1.886 | — | — | 1.823 | 4.586 | 1.012 | 1.823 |
| 7 | x = 3 | 1.886 | 4.631 | 1.003 | 1.820 | 4.586 | 1.015 | 1.820 |

[a] 1 = nLc$_6$Cer; 2 = VI$^6$NeuAcnLc$_6$Cer; 3 = VI$^3$NeuAcnLc$_6$Cer; 4 = III$^3$FucnLc$_6$Cer; 5 = III$^3$FucVI$^6$NeuAcnLc$_6$Cer; 6 = VII$^3$FucX$^3$NeuAcnLc$_{10}$Cer; 7 = III$^3$V$^3$Fuc$_2$VI$^3$NeuAcnLc$_6$Cer

TABLE III

Chemical shifts (ppm from tetramethylsilane) of selected glycosyl H-3 resonances, and coupling constants (Hz) for glycolipids[a] in dimethylsulfoxide-$d_6$ at 328 ± 2 K NeuAcα2 $\longrightarrow$ XGalβ1 $\longrightarrow$ R

| | | H-3$_{eq}$ | H-3 |
|---|---|---|---|
| 1 | — | — | −4.31[b] |
| 2 | x = 6 | 2.638 (4.9,−12.2) | −4.30[c] |
| 3 | x = 3 | 2.755 (4.9,−12.2) | 4.987 (3.2,9.8) |
| 4 | — | — | −4.31[c] |
| 5 | x = 6 | 2.640 (4.9,−12.2) | −4.30[c] |
| 6 | x = 3 | 2.757 (4.9,−12.2) | 3.989 (3.0,9.8) |
| 7 | x = 3 | 2.755 (5.2,−11.9) | 3.980 (3.2,9.8) |

[a] 1 = nLc$_6$Cer; 2 = VI$^6$NeuAcnLc$_6$Cer; 3 = VI$^3$NeuAcnLc$_6$Cer; 4 = III$^3$FucnLc$_6$Cer; 5 = III$^3$FucVI$^6$NeuAcnLc$_6$Cer; 6 = VII$^3$FucX$^3$NeuAcnLc$_{10}$Cer; 7 = III$^3$V$^3$Fuc$_2$VI$^3$NeuAcnLc$_6$Cer

[b] Estimate based on values measured at 338 K (31) and 308 K (32)

[c] Estimates based on value for compound 1, with NeuAcα2 $\longrightarrow$ 6 sialylation-induced shift measured at 308 K (32). 3.291 ppm reported at 308 K for IV$^3$NeuAcnLc$_4$Cer (32).

Several structural features are immediately discernible in the spectrum of the sialylated compounds of the present invention (entry 6 in tables), based on previous studies which have established that type 2 chain neolacto-series glycosphingolipids, bearing terminal NeuAcα2→3/6 and/or Fucα1→3GlcNAc residues, can be successfully analyzed using a set of reproducible "structural reporter group" resonances, and glycosylation induced chemical shift differences derived from standard reference compounds (Levery, S. B. et al. (1986) Carbohydr. Res. 151, 311-328 and Debrowski, J., et al. (1981) Arch. Biochem. Biophys. 210, 405-411).

First, the resonances for α-NeuAc H-3$_{eq}$ at 2.757 ppm ($^2J_{3eq,ax}$=12.2 Hz; $^3J_{3eq,4}$=4.9 Hz), NAc at 1.886 ppm, and β-Gal H-3 at 3.989 ppm ($^3J_{2,3}$=9.8 Hz; $^3J_{3,4}$=3.0 Hz), are diagnostic for a terminal NeuAcα2→3Galβ1 structure (compare values for NeuAcα2→6Galβ1 structures in Tables II and III). The subterminal β-Gal H-1 can just be discerned, under the impurity derived triplet, at the expected shift of 4.214 ppm ($^3J_{1,2}$=7.9 Hz). Next, the α-Fuc H-1 at 4.875 ppm ($^3J_{1,2}$=4.3 Hz), H-5 at 4.586 ppm ($^3J_{5,6}$=6.7 Hz), and $CH_3$ at 1.012 ppm are diagnostic for a single Fucα1→3GlcNAc structure (Levery, S. B. et al. (1986) Carbohydr. Res. 151, 311-328), which furthermore must be located, not on the GlcNAc closest to the non-reducing terminal, but at least one GlcNAc residue further towards the reducing end, otherwise, the H-5 and $CH_3$ resonances would be found at different chemical shifts (see, for example entry 7, Table II) (Levery, S. B., et al., (1986) Carbohydr. Res. 151, 311-328). Consistent with this proposal, there is found an H-1 resonance, for the β-GlcNAc to which the α-Fuc is attached, at 4.739 ppm ($^3J_{1,2}$=7.9 Hz), and another, at 4.340 ppm ($^3J_{1,2}$=6.7 Hz), for the internal Galβ1→4 residue vicinally linked to the same GlcNAc (Levery, S. B., et al., (1986) Carbohydr. Res. 151, 311-328).

The two proton resonance at 4.676 ppm ($^3J_{1,2}$=7.3 Hz) is in the typical range for H-1 of β-GlcNAc of repeating, internal, unbranched N-acetyllactosamine units (Levery, S. B., et al., (1986) Carbohydr. Res. 151, 311-328; Dabrowski, J., et al, (1980) Biochemistry 19, 5652-5658; Dabrowski, J., et al, (1981) Arch. Biochem. Biphys. 210, 405-411; and Dabrowski, U. et al. (1984) J. Biol. Chem. 259, 7648-7651). The signal at 4.170 ppm ($^3J_{1,2}$=7.3) can be assigned to the reducing β-Glc residue (Levery, S. B., et al. (1986) Carbohydr. Res. 151, 311-328; Dabrowski, J., et al. (1980) Biochemistry 19, 5652-5658; Dabrowski, J. (1981) Arch. Biochem. Biphys. 210, 405-411; Dabrowski. U. et al. (1984) J. Biol. Chem. 259, 7648-7651; (Hanfland, P., et al. (1981) Biochemistry 20, 5310-5319) and Koerner, T. A. W. Jr. et al. (1981) Biochemistry 22, 2676-2687). To go with these, a group of three overlapping resonances at about 4.28 ppm are at the typical shifts for β-Gal residues of internal. unbranched lactosyl and/or N-acetyllactosaminyl units (Levery, S. B., et al., (1986) Carbohydr. Res. 151, 311-328; Dabrowski, J., et al. (1980) Biochemistry 19, 5652-5658; Dabrowski, J., et al. (1981) Arch. Biochem. Biphys. 210, 405-411 and Dabrowski, U. et al. (1984) J. Biol. Chem. 259, 7648-7651). Finally, the signal at 4.692 ppm($^3J_{1,2}$=7.3 Hz) can be assigned as follows: It is known that NeuAc 2→3 substitution on the terminal β-Gal of type 2 chain structures induces an upfield shift for H-1 of the nearest β-GlcNAc, which was found on average to be −0.019 ppm at 308K (compare value of −0.016 ppm for the conversion of compound 1 to 3 at 328K. Table I). It is also known that addition of a Fucα1→3 unit to β-GlcNAc of type 2 chain structures induces a downfield shift for H-1 of the next β-GlcNAc towards the nonreducing end, on the order of +0.028 ppm at 328K (see conversion of compound 1 to 4, taken from Levery, S. B., et al. ((1986) Carbohydr. Res. 151, 311-328); compare value of +0.024 ppm for conversion of compound 3 to 5, Table I). Applying both of these induced shifts to the value for H-1 of unsubstituted internal β-GlcNAc found in this spectrum gives a 4.676−0.016+0.028=4.688 ppm, extremely close to 4.692 ppm. One could therefore propose the terminal structure NeuAcα2→3Galβ1→4GcNAcβ1→3Galβ1-→4(Fucα1→3)GlcNAcβ1→3 to explain the shift of this resonance. The complete carbohydrate structure would therefore be as drawn above the spectrum in FIG. 4, with the resonance assignments as shown. It is of course desirable that such a structural proposal, based only on a one-dimensional proton NMR spectrum, should be verified by other available analytical methods.

Other features of the NMR spectrum are the appearance of vinyl proton signals from unsaturated d18:1 (and/or d20:1) sphingosine (R-4 and R-5, FIG. 4), and of H-2 resonances from non-hydroxylated fatty acids. This type of ceramide is consistent with the appearance of the Glc H-1 resonance at 4.170 ppm, since other types of ceramide are known to shift this signal downfield (Levery, S. B., et al. (1986) Carbohydr. Res. 151, 311-328).

Methylation Analysis by Gas Chromatography-electron Impact Mass Spectrometry (GC/EI-MS) and Positive Ion Fast Atom Bombardment Mass Spectrometry (+FAB-MS). Following separation into faster and slower migrating fractions, a portion (about 100 μg) of each of the sialylated compounds of the present invention was permethylated (Hakomori, S. (1964) J. Biochem. (Tokyo) 55, 205-208), and 20% of this was recombined, hydrolyzed in 0.5N $H_2SO_4$/90% acetic acid, reduced with $NaB^3H_4$, and acetylated according to published procedures (Leery, S. B. and Hakomori, S. (1987) Meth. Enzymol. 138, 13-25).

Partially O-methylated, N-methylated deoxyhexitol, hexitol, and hexosaminitol acetates were analyzed by GC/EI-MS using a Hewlett-Packard 5890A gas chromatograph interfaced to a 5970B mass selective detector under the following conditions: Separation was on a 30M DB-5 (J&W Scientific, Rancho Cordova, Calif.) bonded phase fused silica capillary column (temperature program, 140° to 250° C. at 4° C./min) using splitless injection. Electron impact mass spectra were acquired from 50 to 500 atomic mass units at 0.95 s/scan.

Derivatives were identified by characteristic fragmentation patterns (Bjorndal, H. et al. (1970) Angew. Chemi Int. Ed. Eng. 9, 610-619; Jansson, P.-E., et al. (1976) Chem. Commun. Univ. Stockholm 8, 1-75: Stellner, K., et al. (1973) Arch. Biochem. Biophys. 155, 464-472; Stoffel, W. and Hanfland, P. (1973) Hoppe-Seyler's Z. Physiol. Chem. 354, 21-31; and Tai, T., et al., (1975) J. Biochem. (Tokyo) 78, 679-686) and retention times, verified by coinjection with standards when necessary.

Figure 6:
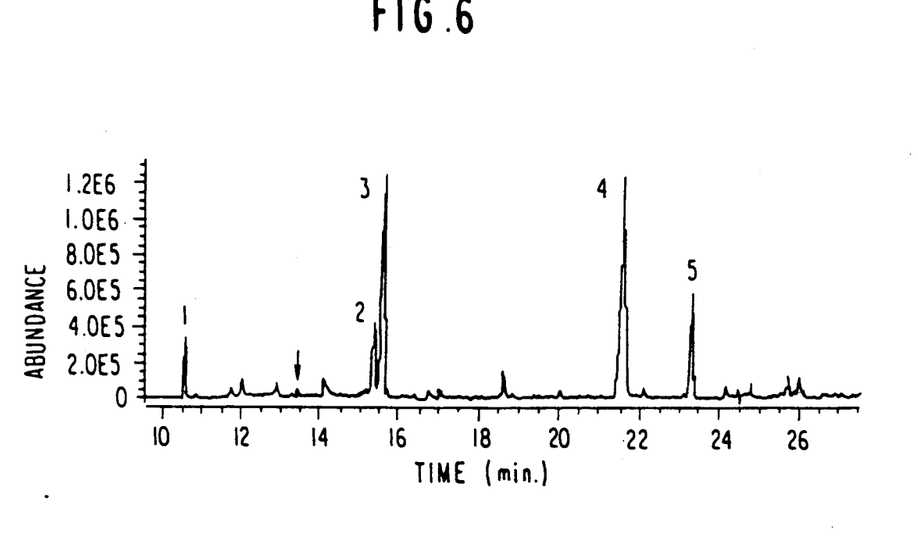
FIG. 6 is an electron impact limited mass chromatogram of monodeuterated partially O-methylated deoxyhexitol, hexitol and hexosaminitol acetates obtained from the hydrolysis of permethylated sialylated compounds of the present invention. The gas chromatography-electron impact mass spectrum is plotted as a composite of relevant structured ions: ordinate, summation of selected ion intensities: abscissa, retention time in minutes. Peaks identified were: 1, 2,3,4-tri-O-Me-Fuc: 2, 2,3,6-tri-O-Me-Glc; 3, 2,4,6-tri-O-Me-Gal: 4, 3,6-di-O-Me-GlcNAcMe; 5, 6-mono-O-Me-GlcNAcMe. The arrow indicates the elution position of 2,3,4,6-tetra-O-Me-Gal.

The results are shown in FIG. 6 which is an electron impact limited mass chromatogram of the treated sialylated compound.

As can be seen from FIG. 6, this procedure detected 2,3,4-tri-O-Me-Fuc; 2,3,6-tri-O-Me-Glc; 2,4,6-tri-O-Me-Gal; 3,6-di-O-Me-GlcNAcMe; and 6-mono-O-Me-GlcNAcMe. These derivatives are consistent with the proposed type 2 chain linkage pattern. Significantly absent is 2,3,4-tri-O-Me-Gal, which would be produced if the terminal α-NeuAc were linked 2→6 rather than 2→3 to the penultimate β-Gal residue; this is consistent with the $^1$H-NMR spectrum. Although it would be impossible to tell from the appearance of the 6-mono-O-Me-GlcNAcMe whether it was derived from a Fucα1→3(Galβ1→4)GlcNAc-β1→ or a Fucα1→4-(Galβ1→3)GlcNAcβ1→ structure, the H$^1$-NMR spectrum unequivocally indicates the former.

The remainder of the permethylated glycolipids were analyzed by +FAB-MS using a JEOL HX-110 mass spectrometer/DA-5000 data system (JEOL Ltd. Tokyo). 20-30 μg of permethylated ganglioside in a thioglycerol/glycerol matrix was bombarded with a Xenon beam source. Acceleration voltage was 10 KV, resolution, 3000. Data was acquired in the accumulation mode from 100 to 4000 a.m.u. with a scan slope of one minute 15 seconds. Cesium iodide/potassium iodide was used as the mass calibration standard.

Figure 5:
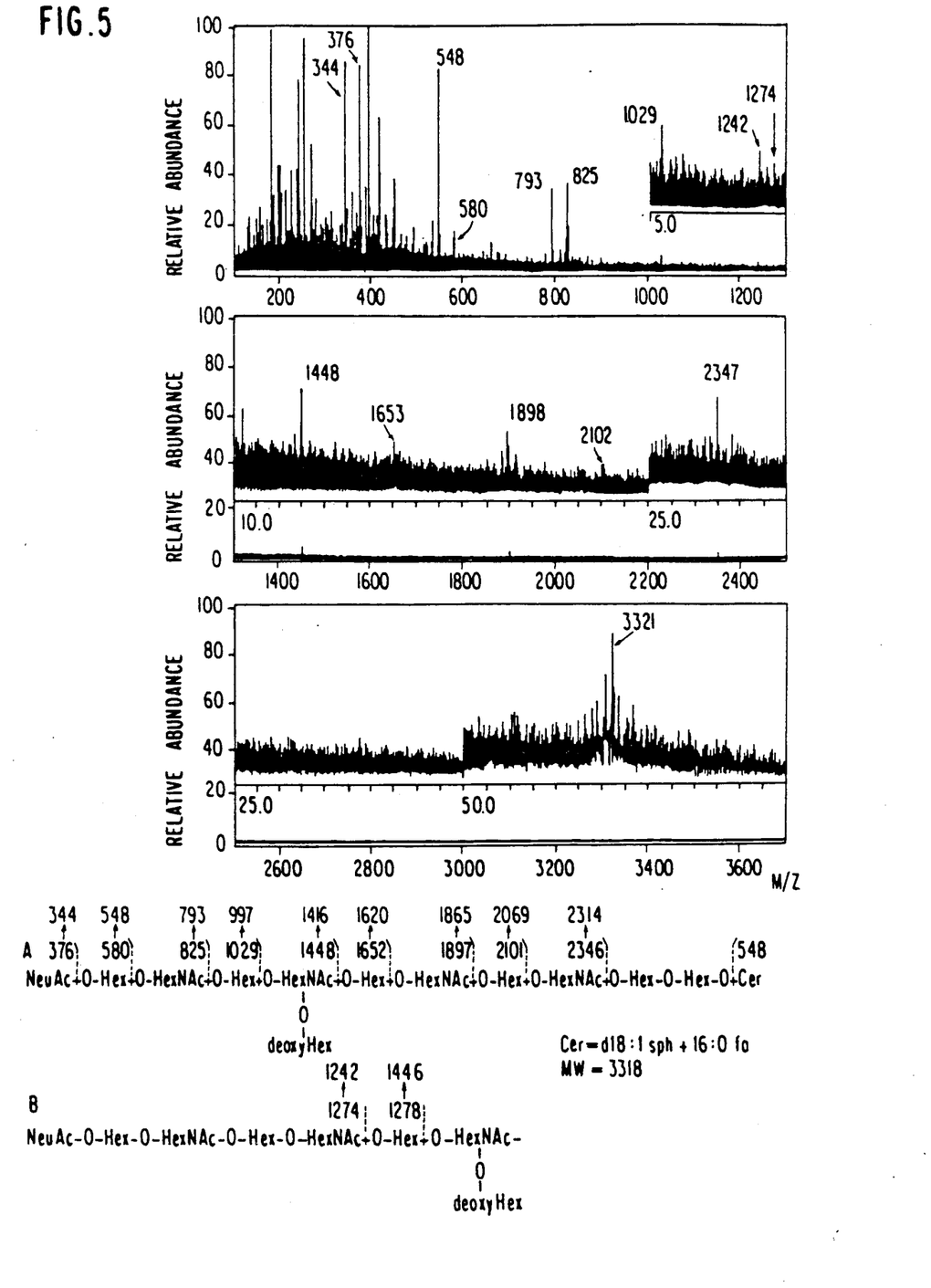
FIG. 5 is a positive ion fast atom bombardment mass spectrum of the permethylated slower migrating sialylated compound fraction with a proposed fragmentation scheme. Nominal, monoisotopic masses were calculated for fragments in the scheme, while masses indicated in the spectrum are those actually measured for the largest peak in each cluster, rounded off to the nearest unit mass.

The results are shown in FIG. 5 which reproduces the mass spectrum of the slower migrating component. The predominant pseudomolecular ion (MH+, nominal mass 3319 a.m.u.) is consistent with the sugar composition NeuAc.deoxyHex.Hex$_6$.HexNAc$_4$ plus a ceramide consisting of d18:1 sphingosine and 16:0 fatty acid. The corresponding ceramide ion is found abundantly at m/z 548. The remainder of the spectrum clearly displays fragments produced by cleavage at glycosyl linkages, preferentially at N-acetylhexosaminyl linkages, with charge retention on the non-reducing portions (Egge, H. and Peter-Katalinic, J. (1987) Mass Spectrom. Rev. 6, 331-393; Fukuda, M. N. et al., (1985) J. Biol. Chem. 260, 1067-1082; Fukuda, M. N. et al., (1986) J. Biol. Chem. 261, 2376-; 2383 Fukuda, M. N. et al., (1986) J. Biol. Chem. 261, 5145-5153 and Hanfland, P., et al. (1984) Eur. J. Biochem. 145, 531-542). These confirm the proposed sugar sequence, residue by residue, as shown in the fragmentation scheme (A). Of particular importance are the prominent ions at m/z 825 and 1448, along with the absence of an ion at m/z 999 representing NeuAc.-deoxyHex.Hex.HexNAc, which unambiguously place the deoxyHex (Fuc) residue on the second HexNAc (GlcNAc) in from the nonreducing end. A less abundant ion at m/z 1274 may represent a minor component, not detectable in the NMR spectrum, in which the deoxyHex residue is absent from the second HexNAc as well (scheme B).

The mass spectrum of the faster migrating component (not shown) was essentially the same, except that the predominant pseudomolecular ions were found at m/z 3431 and 3433. representing species with 24:1 and 24:0 fatty acids (MH+, nominal mass 3429 and 3431 a.m.u. respectively).

Taken together, the H$^1$-NMR, +FAB-MS, and GC/EI-MS data clearly define the linkage positions, sequence, and anomericity of all monosaccharide units of the sialylated compound; predominant ceramide types are also indicated by MS and NMR data.

Figure 7:
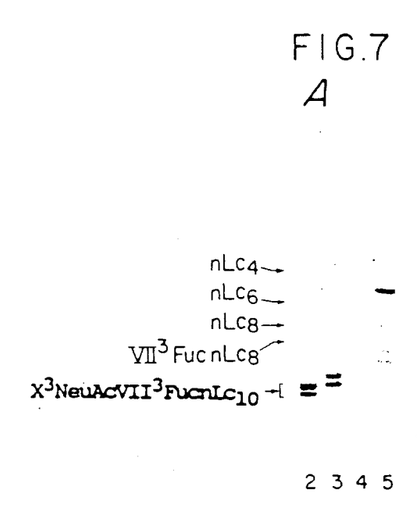

Assessment of Glycolipid Structure by Enzymatic and Chemical Degradation—Both NMR and mass spectrometry clearly indicated that the sialylated compound of the present invention has a long unbranched type 2 chain lactonordecaosylceramide having α1→3 fucosyl substitution at VII GlcNAc. The structure of the sialylated compound was further assessed by sequential degradation with enzymes. Desialylation of the ganglioside with sialidase (Perfringens, Type X, Sigma Chemical Co.) resulted in a 1B2 positive glycolipid (FIG. 7. Panel D. lane 3). The 1B2 reactivity of this compound was abolished by treatment with jackbean β-galactosidase (Panel D, lane 4). When the compound was sequentially treated with sialidase, jackbean β-galactosidase, and jackbean β-N-acetylhexosaminidase, it became positive with an anti-Le$^x$ antibody (Panel C., lane 5), and had the same mobility as $Z_1$ glycolipid (Panel C, lane 6). The ACFH-18 positive neutral glycolipid core, after removal of the fucosyl residue by bovine kidney α-fucosidase or by trichloroacetic acid treatment gave a glycolipid product completely unreactive with ACFH-18.

Reactivity of the Sialylated and Desialylated Compounds of the Present Invention with Monoclonal Anti- body ACFH-18—The reactivity of the sialylated and desialylated compounds of the present invention with monoclonal antibody ACFH-18 was the same and unexpectedly greater than the reactivity of other related compounds (e.g. III$^3$FucnLc$_6$, nLc$_{10}$, VII$^3$FucnLc$_9$ and VII$^3$FucV$^3$FucIII$^3$FucnLc$_8$) with ACFH-18. Data not shown.

While the invention has been described in detail and with reference to specific embodiments thereof, it will be apparent to one skilled in the art that various changes and modifications can be made therein without departing from the spirit and scope thereof.

What is claimed is:

1. A substantially pure unbranched ceramide polysaccharide type 2 chain compound having the following structure:

wherein Gal represents galactose. GlcNAc represents N-acetylglucosamine. Fuc represents fucose, Glc represents glucose and Cer represents ceramide.

2. A substantially pure unbranched ceramide polysaccharide type 2 chain compound having the following structure:

wherein Gal represents galactose, GlcNAc represents N-acetylglucosamine, Fuc represents fucose, Glc represents glucose, Cer represents ceramide and NeuAc represents sialic acid.

* * * * *

UNITED STATES PATENT AND TRADEMARK OFFICE
CERTIFICATE OF CORRECTION

PATENT NO. : 5,030,723

DATED : July 9, 1991

INVENTOR(S) : Edward Nudelman et al.

It is certified that error appears in the above-identified patent and that said Letters Patent is hereby corrected as shown below:

Col. 1, line 1, After the Title and before the Field of Invention, please insert and center --Portions of the invention(s) disclosed herein were supported in part by a grant from the National Cancer Institute, Department of Health and Human Services.--

Signed and Sealed this

Ninth Day of February, 1993

Attest:

STEPHEN G. KUNIN

Attesting Officer

Acting Commissioner of Patents and Trademarks